(12) United States Patent
Okamoto et al.

(10) Patent No.: US 6,566,572 B2
(45) Date of Patent: May 20, 2003

(54) PROCESS FOR PRODUCING 9,10-DIPHENYLANTHRACENE

(75) Inventors: Kuniaki Okamoto, Saitama (JP); Tomimasa Kurita, Saitama (JP); Atsunori Sano, Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 157 days.

(21) Appl. No.: 09/788,550

(22) Filed: Feb. 21, 2001

(65) Prior Publication Data

US 2002/0162991 A1 Nov. 7, 2002

(30) Foreign Application Priority Data

Mar. 6, 2000 (JP) ........................................ 2000-059985

(51) Int. Cl.$^7$ ................................................ C07C 1/28
(52) U.S. Cl. ....................................................... 585/469
(58) Field of Search ......................................... 585/469

(56) References Cited

PUBLICATIONS

Stanforth, Stephen P.; "Catalytic Cross–coupling Reactions in Biaryl Synthesis"; Tetrahedron, 54, (1998), pp. 263–303.
W. Schlenk et al.; Ber. (1928) 61,1675 Discussed in the specification. No English.

W. Steglich et al.; Synthesis (1977) 252. Discussed in the specification. No English.

C. K. Bradsher et al.; Am. Soc. (1943) 65, 451.

Y. Aoyama et al.; Supramolecular Chemistry, vol. 4, pp. 229–241.

S. C. Dickerman et al.; J. Org. Chem. 29, 1964.

Journal of Shanxi University (Nat.Sci. Ed) (19(2), 174, 1996. No English.

Derwent WPI—Patent Abstract of Japan No. JP10017531 (Jan. 20, 1998).

Derwent WPI—Patent Abstract of Japan No. JP7125753 A (May 16, 1995).

Derwent WPI—Patent Abstract of Japan No. JP 9278676 A (Oct. 28, 1997).

*Primary Examiner*—Thuan D. Dang
(74) *Attorney, Agent, or Firm*—Armstrong, Westerman & Hattori, LLP

(57) ABSTRACT

9,10-Diphenylanthracene, which can be produced applicably for industrial use in one or two process steps by subjecting a 9,10-dihalogenoanthracene and a metal or half-metal phenyl compound to a cross-coupling reaction.

6 Claims, No Drawings

PROCESS FOR PRODUCING 9,10-DIPHENYLANTHRACENE

BACKGROUND OF THE INVENTION

The present invention relates to a process for producing 9,10-diphenylanthracene useful as a material for organic electroluminescence (EL) and a material for electrophotograph.

9,10-Diphenylanthracene has widely been known as a material for organic electroluminescence or a material for electrophotograph.

As a process for producing a 9,10-diphenylanthracene, there have been known ① a method comprising reacting benzophenone with calcium hydride to give the object compound (Ber. (1928) 61, 1675), ② a method comprising reacting 9,10-dichloroanthracene with maleic anhydride and then reacting the resultant with aluminum chloride to give the object compound (Ber. (1931) 64, 2194), ③ a method comprising reacting benzoylhydrazide ($C_6H_5CONHNH_2$) with benzoyl formic acid ($C_6H_5COCOOH$), condensing the resultant under dehydration by using dicyclohexyl carbodiimide (DCC), followed by conducting Diels-Alder reaction using benzyne to give the object compound (Synthesis (1977) 252), and ④ a method comprising reacting o-chlorotriphenylmethane with copper cyanide to give a nitrilized product, then subjecting the resultant to Grignard reaction using phenyl magnesium halide and then reacting the product with hydrogen bromide and acetic acid to give the object compound (Am. Soc. (1943) 65, 451), etc. However, all of those methods have some problems that the reaction temperature is too high, the reaction has a lot of process steps, the reaction time is too long and waste substances (such as $Ca(OH)_2$ in ①, Al in ② and dicyclohexyl urea in ③ are generated, and the object compounds obtained by those methods are low purity and those yield is also low such as 50% or less, and therefore any of those methods cannot be said as an industrially applicable method.

Under the circumstances, it has been desired at present to develop a simple and industrially applicable process for producing 9,10-diphenylanthracene.

SUMMARY OF THE INVENTION

The present invention has been accomplished under the circumstances as mentioned above and the object is to provide a process for producing 9,10-diphenylanthracene simply and applicably for industrial use.

The present invention relates to a process for producing 9,10-diphenylanthracene comprising subjecting 9,10-dihalogenoanthracene and a metal or half-metal phenyl compound to a cross-coupling reaction.

That is, the present inventors have earnestly investigated for the purpose of looking for a simple and industrially applicable process for producing 9,10-diphenylanthracene to reach finding that the above-mentioned problems with which known methods have so far been encountered can be solved and the object 9,10-diphenylanthracene can be produced applicably for industrial use in one or two process steps by subjecting a 9,10-dihalogenoanthracene and a metal or half-metal phenyl compound to a cross-coupling reaction, and the present invention has been accomplished on the basis of this finding.

DETAILED DESCRIPTION OF THE PREFERRED EMBODIMENTS

The 9,10-dihalogenoanthracene of the present invention includes 9,10-dichloroanthracene, 9,10-dibromoanthracene, 9,10-diiodoanthracene, 9-bromo-10-chloroanthracene, 9-bromo-10-iodoanthracene, 9-chloro-10-iodoanthracene, etc., among which 9,10-dichloroanthracene, 9,10-dibromoanthracene and 9,10-diiodoanthracene are preferable.

The metal or half-metal phenyl compound is one in which a phenyl group is directly bound to a metal or half-metal atom, and includes one shown by the general formula [1]

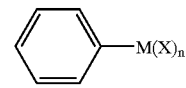

[1]

wherein M is a metal or half-metal atom, X is a halogen atom or a hydroxyl group, and n is an integer of 0 to 2.

In the general formula [1], the metal atom shown by M includes a lithium atom, a magnesium atom, an aluminum atom, a copper atom, a zinc atom, a tin atom, etc., among which a lithium atom, a magnesium atom and a zinc atom, particularly a magnesium atom, are preferable.

The half-metal atom shown by M includes one which is classified into non-metallic but shows metallic properties, which is exemplified by a boron atom, a silicon atom, etc., among which a boron atom is preferable.

The halogen atom shown by X includes a fluorine atom, a chlorine atom, a bromine atom, an iodine atom, etc.

Specific examples of the metal or half-metal phenyl compounds are phenyl compounds having a magnesium-carbon bond (Grignard reagent) such as phenylmagnesium bromide, phenylmagnesium chloride and phenylmagnesium iodide, phenyl compounds having a zinc-carbon bond such as phenylzinc bromide and phenylzinc chloride, phenyl compounds having a lithium-carbon bond such as phenyl lithium, phenyl compounds having a boron-carbon bond such as phenylboric acid, etc., among which phenylmagnesium bromide, phenylmagnesium chloride, phenylmagnesium iodide and phenylboric acid are preferable.

The process for producing 9,10-diphenylanthracene of the present invention is specifically conducted as follows.

The 9,10-dihalogenoanthracene is allowed to react with the metal or half-metal phenyl compound in a suitable solvent, in the presence of, if necessary, a metallic catalyst for a cross-coupling reaction.

In subjecting the 9,10-dihalogenoanthracene and a metal phenyl compound to a cross-coupling reaction, the metal phenyl compound which is previously prepared may be subjected to the reaction, or a metal and a phenyl halide, which are starting materials for the metal phenyl compound, may be reacted at the same time with the 9,10-dihalogenoanthracene. In the latter case, the metal phenyl compound in the present invention is once produced in a reaction system and then this reaction product is subjected to the cross-coupling reaction to give the object compound. The reaction formulas are shown below.

The process for producing objective 9,10-diphenylanthracene by reacting the metal phenyl compound prepared preciously with the 9,10-dihalogenoanthracene is shown in the following formula [2].

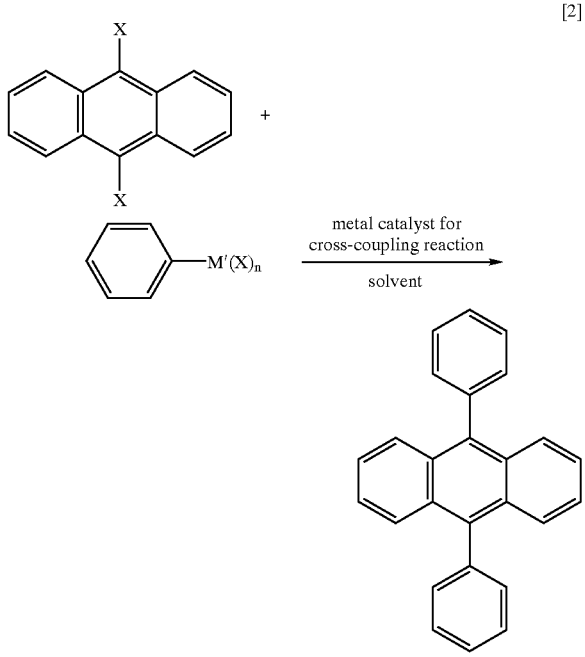

wherein M' is a metal atom, and X and n have the same meaning as above.

The process for producing the object compound by reacting a metal and phenyl halide at the same time with the 9,10-dihalogenoanthracene is shown in the following formula [3].

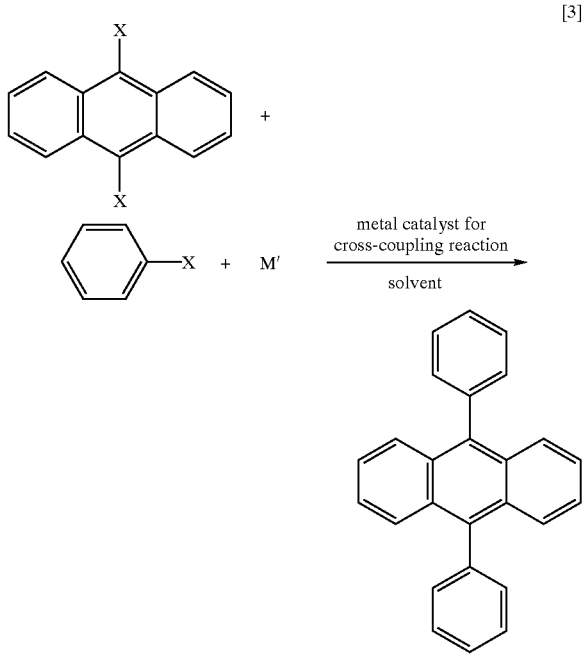

wherein M', X and n are as defined above.

An amount of the metal or half-metal phenyl compound to be used depends on the kind of the 9,10-dihalogenoanthracene to be used and the amount is generally 1 to 4 equivalent, preferably 1 to 2 equivalent, relative to the 9,10-dihalogenoanthracene.

The reaction solvent includes an aromatic hydrocarbon such as toluene, xylene and benzene, an ester such as methyl acetate, ethyl acetate and butyl acetate, an ether such as diethyl ether, tetrahydrofuran, dioxane, dimethoxy ethane and diisopropyl ether, a hydrocarbon halide such as methyl chloride, chloroform, dichloromethane, dichloroethane and dibromoethane, a ketone such as acetone and methylethyl ketone, an amide such as dimethylformamide, a nitrile such as acetonitrile, dimethylsulfoxide, etc. The solvent may be used alone or in a combination of two or more thereof.

The metallic catalyst for the cross-coupling reaction is not specifically limited so far as it shows this effect, and includes a palladium type catalyst, a nickel type catalyst, an iron type catalyst, a cobalt type catalyst, a ruthenium type catalyst, a rhodium type catalyst, etc., among which a 0- or 2-valent palladium type catalyst such as palladium bromide, palladium chloride, palladium iodide, palladium cyanide, palladium acetate, palladium trifluoroacetate, palladium acetyl acetonato [$Pd(acac)_2$], diacetate bis (triphenylphosphine) palladium [$Pd(OAc)_2(PPh_3)_2$], tetrakis (triphenylphosphine) palladium [$Pd(PPh_3)_4$], tris (dibenzylideneacetone) dipalladium [$Pd_2(C_6H_5CH=CHCOCH=CHC_6H_5)_3$], dichlorodiamine palladium [$Pd(NH_3)_2Cl_2$], dichloro bis (acetonitrile) palladium [$Pd(CH_3CN)_2Cl_2$], dichloro bis (benzonitrile) palladium [$Pd(PhCN)_2Cl_2$], dichloro [1,2-bis (diphenylphosphino) ethane] palladium [$Pd_2(dppe)Cl_2$], dichloro [1,1-bis (diphenylphosphino) ferrocene] palladium [$Pd(dppf)Cl_2$], dichloro bis (tricyclohexylphosphine) palladium [$Pd[P(C_6H_{11})_3]_2Cl_2$], dichloro bis (triphenylphosphine) palladium [$Pd(PPh_3)_2Cl_2$], dichloro his (tri-o-tolylphosphine) palladium [$Pd[P(CH_3C_6H_4)_3]_2Cl_2$], dichloro bis (1,5-cyclooctadiene) palladium [$Pd(C_8H_{12})_2Cl_2$] and dichloro bisacetonitrile (triphenylphosphine) palladium [$Pd(PPh_3)(CH_3CN)_2Cl_2$], a 0- or 2-valent nickel type catalyst such as nickel bromide, nickel chloride, nickel fluoride, nickel iodide, nickel hydroxide, nickel acetate, nickel hydroxyacetate, nickel acetyl acetonato [$Ni(acac)_2$], nickel trifluoroacetyl acetonato [$Ni(CF_3COCHCOCH_3)_2$], nickel hexafluoroacetyl acetonato [$Ni(CF_3COCHCOCF_3)_2$], bis (2,2,6,6-tetramethyl-3,5-heptanedionato) nickel [$Ni(C_{11}H_{19}O_2)2$], bis (cyclopentadienyl) nickel [$Ni(C_5H_5)_2$], bis (ethylcyclopentadienyl) nickel [[$Ni(C_2H_5)(C_5H_4)]_2$], bis (i-propylcyclopentadienyl) nikel [[$Ni(C_3H_7)C_5H_4]_2$], bis (tetramethylcyclopentadienyl) nickel [[$Ni(CH_3)_4C_5H)]_2$], bis (pentamethylcyclopentadienyl) nickel [[$Ni(CH_3)_5C_5]_2$], bis (1,5-cyclooctadienyl) nickel [$Ni(C_8H_{12})_2$], nickel cyclohexane butyrate [$Ni[OOC(CH_2)_3C_6H_{11}]_2$], nickel dimethyl glyoxirne [$Ni(HC_4H_6N_2O_2)_2$], nickel 2-ethylhexanoate [$Ni[OOCCH(C_2H_5)C_4H_9]_2$], tetrakis (trifluorophosphine) nickel [$Ni(PF_3)_4$], dicarbonyl bis (triphenylphosphine) nickel [$Ni(PPh_3)_2(CO)_2$], dibromo bis (triphenylphosphine) nickel [$Ni(PPh_3)_2Br_2$], dichloro bis (triphenylphosphine) nickel [$Ni(PPh_3)_2Cl_2$], dichloro [1,2-bis (diphenylphosphino) ethane] nickel [$Ni(dppe)Cl_2$], dichloro [1,3-bis (diphenylphosphino)propane] nickel [$Ni(Ph_2PCH_2CH_2CH_2PPh_2)Cl_2$], dichloro bis (2-ethylhexanoate) nickel [$Ni[OOCCH(C_2H_5)C_4H_9]_2Cl_2$], hexaamine nickel chloride [[$Ni(NH_3)_6$]$Cl_2$], hexaamine nickel iodide [[$Ni(NH_3)_6$]$I_2$] and nickelocene, a divalent iron type catalyst such as ferric chloride and ferrocene, a divalent cobalt type catalyst such as cobalt chloride, cobalt bromide, cobalt acetate, cobalt acetyl acetonato [$Co(acac)_2$] and cobaltcene, a divalent copper type catalyst such as copper chloride, a divalent ruthenium type catalyst such as dichloro tris (tyriphenylphosphine) ruthenium [$RuCl_2(PPh_3)_3$], a monovalent rhodium type catalyst such as chloro tris (triphenylphosphine) rhodium [RhCl(PPh$_3$)$_3$], etc. among which 0- or 2-valent palladium type catalyst, 0- or 2-valent nickel type catalyst, etc. are preferable. The catalyst may be carried on a porous carrier, a polymer which may be cross-linked, etc., and the porous carrier includes carbon, alumina, zeolite, silica, celite, etc.

An amount of the metallic catalyst for the cross-coupling reaction to be used depends on the kinds of the 9,10-dihalogenoanthracene and the metal or half-metal phenyl compound to be used, and it is generally 0.00001 to 1 mole part, preferably 0.0001 to 0.3 mole part, relative to mole part of the 9,10-dihalogenoanthracene.

A reaction temperature is generally 0 to 200° C., preferably 20 to 150° C., because when it is too high, control of the reaction becomes difficult and when it is too low, the reaction speed becomes slow and thus a long time is required for the reaction.

A reaction time depends on the reaction temperature and the kinds of the metal or half-metal phenyl compound, the metallic catalyst for the coupling reaction, etc., and it is generally 1 minute to 12 hours, preferably 10 minutes to 1 hour.

Reaction operations and after-treatments other than those mentioned above may be conducted after those generally used in similar reactions.

As the metal or half-metal phenyl compound, a commercially available product or one prepared by a conventional manner may be used.

As mentioned above, the present invention relates to a process for producing highly purified 9,10-diphenylanthracene at high yield by 1 or 2 process steps, and this method has such advantages that the reaction conditions including the reaction temperature, the reaction time, etc. are suitable to industrial point of view and an amount of waste substance is small.

In the following, the present invention is further explained in details referring to Examples, but it is not limited thereto by any means.

EXAMPLE

Example 1

In suspension of 49.8 g (2.04 mol) of Mg and 1.0 L of THF was dropwisely added 321.4 g (2.04 mol) of bromobenzene under refluxing to give Grignard reagent. Thus prepared Grignard reagent was dropwisely added to a mixed solution of 286 g (0.85 mol) of 9,10-dibromoanthracene, 566mL of THF and 0.6 g (0.00085 mol) of Pd(PPh$_3$)$_2$Cl$_2$ with agitation at 30 to 60° C. in 30 minutes, followed by agitation at the same temperature for 1 hour. To the reaction solution was added 300 ml of diluted hydrochloric acid and the object substance was extracted with 3 L of toluene. The obtained organic layer was washed with saturated saline solution and concentrated to 750 mL in total. The precipitated crystal was recovered by filtration and dried at 70° C. for 1 hour to give 229.5 g of 9,10-diphenylanthracene (yield 81.7%, HPLC purity 97.7%).

Example 2

In suspension of 49.8 g (2.04 mol) of Mg and 1.0 L of THF was dropwisely added 229.6g (2.04 mol) of chlorobenzene under refluxing to give Grignard reagent. Thus prepared Grignard reagent was dropwisely added to a mixed solution of 210 g (0.85 mol) of 9,10-dichloroanthracene, 566 mL of THF and 1.0 g (0.00085 mol) of Pd(PPh$_3$)$_4$ with agitation at 30 to 60° C. in 30 minutes, followed by agitation at the same temperature for 1 hour. To the reaction solution was added 300 ml of diluted hydrochloric acid and the object substance was extracted with 3 L of toluene. The obtained organic layer was washed with saturated saline solution and concentrated to 750 mL in total. The precipitated crystal was recovered by filtration and dried at 70° C. for 1 hour to give 246.6 g of 9,10-diphenylanthracene (yield 87.8%, HPLC purity 98.4%).

Example 3

To a mixed solution of 286.6 g (0.85 mol) of 9,10-dibromoanthracene, 321.4 g (2.04 mol) of bromobenzene and 1.5 L of THF were added 49.8 g (2.04 mol) of Mg and 0.6 g (0.00085 mol) of Pd(PPh$_3$)$_2$Cl$_2$, followed by heating up to refluxing and agitating at the same temperature for 1 hour. To the resultant was added 300 mL of diluted hydrochloric acid and the object substance was extracted with 3 L of toluene. The obtained organic layer was washed with saturated saline solution and concentrated to 750 ml in total. The precipitated crystal was recovered by filtration and dried at 70° C. for 1 hour to give 207.3 g of 9,10-diphenylanthracene (yield 73.8%, HPLC purity 95.2%).

Example 4

To a mixed solution of 286.6 g (0.85 mol) of 9,10-dibromoanthracene, 29.9 g (0.0255 mol) of Pd(PPh$_3$)$_4$ and 3L of benzene was added 1.5L of 2M Na$_2$CO$_3$aq and 1.2 L of ethanol solution of 228.6 g (1.87 mol) of phenyl boric acid, followed by refluxing for 6 hours. To the reaction solution was added 200 mL of 30% H$_2$O$_2$ to terminate the reaction, and an organic layer was recovered. The organic layer was washed with water and dehydrated by anhydrous magnesium sulfate, followed by filtration and concentration of the filtrate to 750 mL in total. The precipitated crystal was filtered and dried to give 212.0 g of 9,10-diphenylanthracene (Yield 75.5%, HPLC purity 97.6%).

Example 5

Grignard reagent prepared by the same manner as in Example 1 was dropwisely added to a mixed solution of 286 g (0.85 mol) of 9,10-dibromoanthracene, 566 mL of THF and 0.24 g (0.00085 mol) of Ni(acac)$_2$ with agitation at 30 to 60° in 30 minutes, followed by agitation at the same temperature for 1 hour. To the reaction solution was added 300 mL of diluted hydrochloric acid and the object substance was extracted with 3 L of toluene. The obtained organic layer was washed with saturated saline solution and concentrated to 750 mL in total. The precipitated crystal was recovered by filtration and dried at 70° C. for 1 hour to give 213.2 g of 9,10-diphenylanthracene (Yield: 75.9%, HPLC purity:97.0%).

Example 6

Grignard reagent prepared by the same manner as in Example 1 was dropwisely added to a mixed solution of 286 g (0.85 mol) of 9,10-dibromoanthracene, 566 mL of THF and 0.4 g (0.00085 mol) of Ni(dppe)Cl$_2$ with agitation at 30 to 60° C. in 30 minutes, followed by agitation at the same temperature for 1 hour. To the reaction solution was added 300 mL of diluted hydrochloric acid and the object substance was extracted with 3 L of toluene. The obtained organic layer was washed with saturated saline solution and concentrated to 750 mL in total. The precipitated crystal was recovered by filtration and dried at 70° C. for 1 hour to give 229.5 g of 9,10-diphenylanthracene (Yield: 81.7%, HPLC purity:97.7%).

Example 7

Grignard reagent prepared by the same manner as in Example 1 was dropwisely added to a mixed solution of 210 g (0.85 mol) of 9,10-dichloroanthracene, 566 mL of THF and 0.6 g (0.00085 mol) of Ni(PPh$_3$)$_2$Br$_2$ with agitation at 30 to 60° C. in 30 minutes, followed by agitation at the same temperature for 1 hour. To the reaction solution was added 300 mL of diluted hydrochloric acid and the object substance was extracted with 3 L of toluene. The obtained organic layer was washed with saturated saline solution and concentrated to 750 mL in total. The precipitated crystal was recovered by filtration and dried at 70° C. for 1 hour to give 228.6 g of 9,10-diphenylanthracene (Yield: 81.4%, HPLC purity:98.2%).

Example 8

To a mixed solution of 286.6 g (0.85 mol) of 9,10-dibromoanthracene, 321.4 g (2.04 mol) of bromobenzene and 1.5 L of THF were added 49.8 g (2.04 mol) of Mg and 0.024 g (0.0085 mol) of Ni(acaC)$_2$, followed by heating up to refluxing and agitating at the same temperature for 1 hour. To the reaction solution was added 300 mL of diluted hydrochloric acid and the object substance was extracted with 3 L of toluene. The obtained organic layere was washed with saturated saline solution and concentrated to 750 mL in total. The precipitated crystal was recovered by filtration and dried at 70° C. for 1 hour to give 247.2 g of 9,10-diphenylanthracene (Yield: 73.5%, HPLC purity: 94.7%).

As mentioned above, the present invention provides a process for producing 9,10-diphenylanthracene simply and industrially, and according to the process, 9,10-diphenylanthracene can be produced by 1 or 2 process steps and the yield and purity of the object substance are higher as compared with conventional methods, and thus this process can be used as an industrial process of production.

What is claimed is:

1. A process for producing 9,10-diphenylanthracene, which comprises subjecting a 9,10-dihalogenoanthracene and a metal or half-metal phenyl compound to a cross-coupling reaction in the presence of a metal catalyst for a cross-coupling reaction to yield 9,10-diphenylanthracene.

2. A process for producing 9,10-diphenylanthracene, which comprises subjecting a 9,10-dihalogenoanthracene and a metal or half-metal phenyl compound shown by the general formula [1]

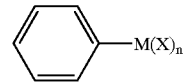

[1]

wherein M is a metal or half-metal atom, X is a halogen atom or a hydroxyl group, and n is an integer of 0 to 2, to a cross-coupling reaction in the presence of a metal catalyst to a cross-coupling reaction to yield 9,10-diphenylanthracene.

3. A process according to claim 2, wherein M is a lithium atom, a magnesium atom, an aluminum atom, a copper atom, a zinc atom, a tin atom, a boron atom or a silicon atom.

4. A process according to claim 1, wherein the 9,10-dihalogenoanthracene is 9,10-dibromoanthracene, 9,10-dichloroanthracene, 9,10-diiodoanthracene, 9-bromo-10-chloroanthracene, 9-bromo-10-iodoanthracene or 9-chloro-10-iodoanthracene, the metal or half-metal phenyl compound is phenylmagnesium bromide, phenylmagnesium chloride, phenylmagnesium iodide, phenylzinc bromide, phenylzinc chloride, phenyl lithium or phenyl boric acid, and the metal catalyst for the cross-coupling reaction is an iron-containing catalyst, a cobalt-containing catalyst, a nickel-containing catalyst, a copper-containing catalyst, a ruthenium-containing catalyst, a rhodium-containing catalyst or a palladium-containing catalyst.

5. A process according to claim 2, wherein the 9,10-dihalogenoanthracene is 9,10-dichloroanthracene or 9,10-dibromoanthracene, the metal or half-metal phenyl compound is phenylmagnesium chloride or phenylmagnesium bromide, and the metal catalyst for the cross-coupling reaction is a nickel-containing catalyst or a palladium-containing catalyst.

6. A process according to claim 1, wherein the metal catalyst for the cross-coupling reaction is an iron-containing catalyst, a cobalt-containing catalyst, a nickel-containing catalyst, a copper-containing catalyst, a ruthenium-containing catalyst, a rhodium-containing catalyst or a palladium-containing catalyst.

* * * * *